United States Patent [19]

Hansen et al.

[11] 4,022,575
[45] May 10, 1977

[54] AUTOMATIC CHEMICAL ANALYZER

[75] Inventors: Elo Harald Hansen, Lyngby; Jaromir Ruzicka, Narum, both of Denmark

[73] Assignee: Block Engineering, Inc., Cambridge, Mass.

[22] Filed: Sept. 15, 1975

[21] Appl. No.: 613,275

[30] Foreign Application Priority Data

Sept. 16, 1974 Denmark .................... 4846/74

[52] U.S. Cl. .................... 23/230 R; 23/253 R; 23/259; 73/425.4 R
[51] Int. Cl.² ................................ G01N 1/14
[58] Field of Search ............ 23/230 R, 253 R, 259; 73/425.4 R

[56] References Cited

UNITED STATES PATENTS

| | | | |
|---|---|---|---|
| 3,241,432 | 3/1966 | Skeggs et al. | 23/253 R |
| 3,320,148 | 5/1967 | Skeggs | 23/253 R |
| 3,424,557 | 1/1969 | Skeggs | 23/253 R |
| 3,427,135 | 2/1969 | Pelavin et al. | 23/253 R |
| 3,572,994 | 3/1971 | Hochstrasser | 23/253 X |
| 3,600,953 | 8/1971 | Isreeli et al. | 23/253 R |
| 3,843,326 | 10/1974 | Lichtenstenen | 23/253 R |

Primary Examiner—R.E. Serwin
Attorney, Agent, or Firm—Schiller & Pandiscio

[57] ABSTRACT

A continuous flow analytical system in which there is provided a continuous unobstructed carrier stream into which discrete volumes of sample solutions to be observed for reaction with the carrier stream are injected successively. A detector for measuring the results of any reaction between the carrier stream and sample solutions is positioned downstream from the point of injection.

9 Claims, 6 Drawing Figures

PRIOR ART

AUTOMATIC CHEMICAL ANALYZER

This invention relates to a method of analysis, based upon discrete, instant sample introduction of an aqueous sample into a continuously, nonhindered flowing stream of an aqueous solution, which solution can contain one or more reagents with which the content of said sample can react chemically, and particularly concerns continuous chemical analysis by quantitative evaluation in a flow-through detector arrangement.

The ever increasing demand for numbers of analyses in clinical, agricultural, pharmaceutical and other types of analytical control has lead to the development of a large number of various instruments for automated analysis. The development in this field is further being stimulated by the additional advantages gained by automation: increased precision, decreased cost per assay and good reliability of the automated equipment. The present trend, however, is aimed at increased sampling rates and simplification of the analyzers. The numerous instruments suggested and developed for analysis of larger number of individual sample solutions can be divided into two groups: batch analyzers and continuous-flow analyzers.

In the batch analyzer each sample is placed in its individual container within which it remains during the course of the analytical procedure. The containers proceed in the instrument on a moving belt, on rails or by similar means, and reagents are added at predetermined points/(times). Finally, when the treated sample reaches the detector unit (spectrophotometer, flame photometer etc.), it is sucked into a flow cell where the actual measuring procedure is executed; thus, every single sample is evaluated separately in the analyzer, i.e., it operates discontinuously. As the individual samples are strictly separated through the entire process, a high sampling rate, and therefore an actual output of analyses even in excess of 150 samples per hour, can be achieved, without the danger of "carry-over" (sample cross-contamination). The disadvantage of batch analyzers is that they contain complex moving parts which eventually become worn during use, and that there might be problems associated with washing and/or discarding the containers after use. Not least of such problems is the lower versatility of these instruments compared to continuous-flow analyzers.

In the continuous-flow analyzers, the samples are successively aspirated from their individual containers into a tube through which the samples move until the entire analysis is completed. In this way, the samples — which successively follow each other — become part of a continuously moving stream into which, at predetermined points/(times) reagents continuously are added at fixed flow rates. The processed stream finally reaches a flow-through cell of a spectrophotometer (or another measuring instrument) where the quantitative measurement is executed and the signal continuously is recorded. The movement of all liquids within the conduits of continuous-flow analyzers is controlled by a pump which also takes care of the aspiration of the samples. The greatest advantage of continuous-flow analyzers is their simplicity and their versatility which allows an easy programming of the flowing stream (which for instance might be split for multiple analysis). The disadvantage of the continuous-flow concept is primarily the potential possibility of carry-over, which matter therefore always must be born in mind so that all necessary precautions can be taken to avoid it. It was in fact the introduction of the air bubble into the flowing stream (L. T. Skeggs, Am. J. Clin. Pathol., 28 (1957) 311) which made the continuous-flow analysis practically applicable. The role of the air bubble is simply to segment the flowing stream and thus minimize the longitudinal mixing occuring in the conduits of continuous-flow analyzers, that is, to minimize the carry-over. Thus, in one commercially available system in which this principle is used, the continuously flowing stream is regularly and frequently segmented by air bubbles which effectively sweep the tubes, thereby allowing the sampling rate to increase up to ca. 100 samples per hour (although 60 samples per hour is the most frequently encountered rate). A further increase of the sampling rate is, however, hindered by the necessity of reaching, during each individual sample measurement, a "steady state" at which the signal can be registered for the purpose of quantitative evaluation. The signal output, as recorded e.g. by a colorimeter through which the continuously flowing stream passes, has as shown in the drawing labelled "Prior Art" the form of a "peak," which reflects a change from a steady baseline state (A) to a sample steady state (B) and vice versa. The transition between these two steady states has been found to obey first-order kinetics and can be characterized by two parameters, the half-wash time ($W_{1/2}$) and the lag phase time (L) (R. E. Thiers, W. J. Kirsch and R. R. Cole, Technicon Symposia 1966, Vol. I. Automation in Analytical Chemistry, p. 37–44). It has been established that a time equivalent to one L plus at least seven $W_{1/2}$ is necessary to come from one steady state to another with a precision better than 1%. Consequently, long sampling times are required in order to achieve the necessary precision of analysis, and the output of the continuous analyzer becomes limited. With a typical $W_{1/2}$ time of 10 seconds and an L-time of 20 seconds, 90 seconds are needed to achieve 99% steady state and another 90 seconds to reach the baseline again. As this would yield a sampling rate of only 20 samples per hour, sampling and wash times are usually cut shorter, but at sampling rates in excess of 60 samples per hour the individual samples will obviously start to influence each other due to carry-over.

In studies of continuous systems and the kinetic parameters characterizing these systems it has been established that all fall and rise curves for a given system are identical in shape and therefore it is not necessary to reach the sample steady state provided that the sample is introduced into the continuously flowing stream over an exactly fixed period of time. Thus, if the sampling time is decreased to three $W_{1/2}$ units, an error of 0.1 $W_{1/2}$ of the sampling period would cause an analytical error of only 2%. This precision of sampling is, however, impossible to achieve in the present commercial system where the sampling is effected by the peristatic pump which sucks the samples from their individual containers and then pumps them further through the system where the samples — following segmentation with air bubbles — at predetermined points/(times) are joined by those reagent solutions required for the particular analysis. The reasons for this are: (a) difficulties with precise timing of the sampling tube from the position "sampling" to the position "wash" and the fact that level of the liquid sample in all sample containers must be identical (otherwise slightly varying amounts of air, and hence sample, will be introduced in the sampling tube); (b) irregularities in the pumping action of the peristaltic pump, caused by the spacing of the rollers pressing the tubes on the platen, manifested by periodical pulsations of all streams; and (c) the presence of the air bubbles which, besides segmenting the stream, also are responsible for the pulsations of the stream due to the compressibility of air.

We have found that the samples to be assayed can be introduced into a continuous-flow analyzer system by injecting them directly into the continuously flowing stream. Unlike the prior art system where the sampling tube continuously introduces material (sample - air - wash - sample etc.) which then joins a flowing stream of reagents, the present invention is based upon discrete injection of a well defined volume of sample into a continuously flowing stream of reagents, said injection being executed in a well defined, short span of time. This discrete, instant sampling creates geometrically well defined segments of sample solution within the flowing stream which then is carried further towards the detector unit. The reagents, necessary for the particular analysis, can be present in the carrier stream into which the samples are being injected, and additional reagents can, if required, be added at positions further down the line on the way to the detector. In order to increase the reaction rate, the sample stream can be preheated and/or, after injection of the samples, heated again. It was found that there is no lag time observable on the response curves obtained by the sample injection technique. More surprisingly, however, it was observed that the discrete injection technique allows attainment of a reproducibility of determination of better than ± 1%, even if the sample is injected for as short a span of time as that corresponding to one $W_{1/2}$ unit (see Examples I and II) (in practice, however, a time equivalent to two $W_{1/2}$ units is recommended in order not to lose too much sensitivity). Even if a value of $W_{1/2}$ of 10 seconds is assumed it would — due to the absence of the lag phase — nevertheless imply that as many as 180 samples could be processed per hour. This very fast sampling rate, which is unusual for continuous-flow systems, brings about another aspect of the present invention.

It has been known for some time (J. R. Gerke and A. Ferrari, Technicon Symposia 1967, Vol. I, Automation in Analytical Chemistry, p. 531-540) that the main role of the air bubbles — while segmenting the stream — is to minimize the problems of mixing as "the presence of air segments causes wall friction, even at low velocities, thus producing turbulent rather than laminar flow." It has also been realized that this desired turbulent flow can be created by increasing the flow rate and decreasing the tube diameter.

Nevertheless, this approach was not considered practically applicable in continuous-flow analysis because the "increased flow increases consumption of reagents and samples and consequently increases the expense of operation. If sufficient sample is not available, the method cannot be used" (Gerke and Ferrari and the reference denoted above). In view of the present invention, which allows high sampling rates, this view-point has to be revised as the volume of reagent per analysis very well might be equal or even smaller for samples injected into the rapidly moving carrier stream than that required in conventional continuous-flow analysis where the samples are introduced continuously and slowly into the carrier stream. Furthermore, only a small volume of sample is required (0.5 ml or less — see also Examples) because the instant sampling creates well defined narrow segments of sample — consequently resulting in well pronounced detector signals.

Thus, the presence of air bubbles in the flowing stream is not necessary any more provided that a turbulent flow characteristic has been obtained and that the length of the conduits of the continuous-flow analyzer is kept to a minimum. In order to appreciate this situation, certain well known disadvantages of the air segmentation should be mentioned. Using conventional volumes and flow patterns of the prior art system, the average sample at a flow rate of 5 ml per minute will occupy approximately 2 meters of tubing, with a total of 100 bubbles segmenting it. Since the air segments are compressible, the real volume of liquid flowing through the tube (and the detector) will vary and an irregular flow will occur. The shorter the sampling is the more serious effect these, self-amplitying, irregularities will product. Furthermore, the presence of the air bubbles complicate the instrumental arrangement. First, the air has to be regularly introduced into the system and therefore a separate pump tube has to be installed. Then, immediately before the detector, the air has to be removed from the flowing stream in order not to distort the signal output. Alternatively, a minicomputer which can cancel the signal while the air bubble is passing through the detector has to be installed.

For these reasons, the instant, discrete sampling as described in this invention should preferably be used on non-air segmented streams; the Examples described hereafter have consequently been chosen to demonstrate the feasability of this invention in such an experimental arrangement. On the other hand, the instant, discrete sampling can also be applied on air segmented carrier streams of reagents, should be reactions proceed to equilibrium so slowly that a long time, and therefore a long line of tubing, is required before the stream ought to reach the detector.

Finally, before turning to Examples, a very practical way of injecting the samples into the carrier stream should be mentioned. The simplest way to execute the instant, discrete sampling is to aspirate the sample into a syringe equipped with a hypodermic needle, which syringe at the same time serves as a pipette for measuring the volume of the sample. The needle then pierces through the wall of an elastic tube at a chosen time and the sample is rapidly injected into the carrier stream flowing through said tube. Mechanical arrangements to facilitate the piercing and injection can readily be visualized, but surprisingly the manual sampling as mentioned in the Examples was found very satisfactory, too. The critical parameters influencing the precision of sampling are mentioned below.

Other objects of the invention will in part be obvious and will in part appear hereinafter. The invention accordingly comprises the apparatus and method possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings wherein.

Figure 1:
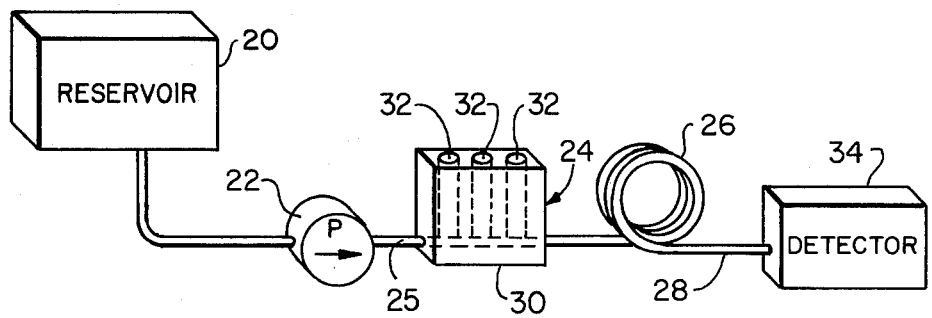
FIG. 1 is a schematic of apparatus embodying the principles of the present invention.
Figure 2B:
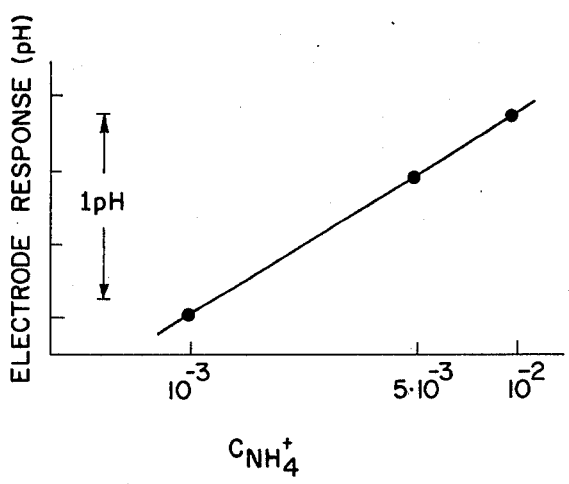
FIGS. 2a and 2b are respectively graphs illustrating operation of the system of FIG. 1 according to Example I and FIGS. 3a, 3b and 3c are respectively graphs illustrating operation of the system according to Example II.

In the apparatus of the invention shown schematically in FIG. 2 the carrier stream, derived from reservoir 20, is pumped by peristaltic pump 22 through a tubing arrangement consisting of three parts: injector 24, mixing coil 26 and transmission tubing 28. Injector 24 located immediately after the peristaltic pump typically comprises rubber tube 25 horizontally situated in a Perspex block 30, the latter being furnished with a series of precisely, vertically bored holes 32 into which a hypodermic needle and the part of the syringe adjacent to the needle can be conveniently placed. The size of block 30, the hole diameters and their relative positions are chosen so that when a syringe is pressed into the holder, the hypodermic needle will pierce through the rubber tube, placing the orifice of the needle right in the middle of the continuously flowing carrier stream. After injection of the sample, the needle can be removed from the tube as the hole in the rubber tube will close itself due to the elastic properties of the material. Mixing coil 26 is typically a one meter long glass tube, wound into a coil of ca. 3 cm in diameter. Transmission tubing 28 is typically a short piece of PVC tubing which serves to connect the mixing coil with detector unit 34. The latter, as will be seen, can be any of a number of known devices.

EXAMPLE I

Automated determination of the ammonium content in ammonium chloride solutions by potentiometric measurements.

Figure 2A:
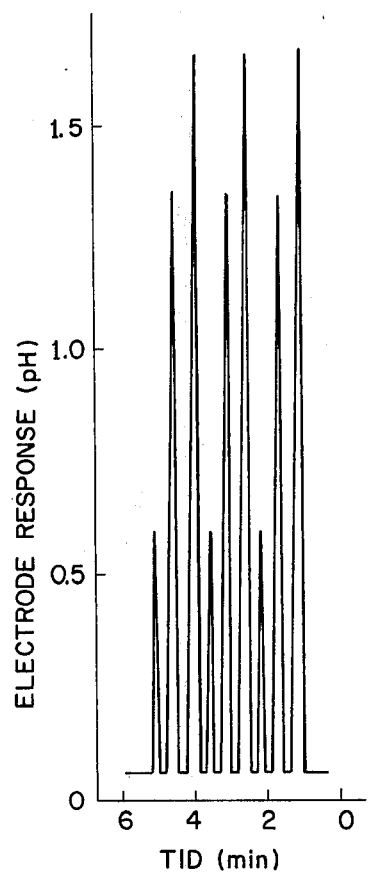

The carrier stream, which consisted of a 0.05 M aqueous solution of NaOH, was pumped at a rate of 10 ml per minute through a tubing arrangement of internal diameter 2 mm by means of a peristaltic pump. Aqueous samples of ammonium chloride ($1.0\times10^{-3}$M; $5.0\times10^{-3}$M; and $1.0\times10^{-2}$M, respectively), each of a volume of 0.50 ml, were contained within disposable plastic syringes equipped with 10 mm long hypodermic needles (outer diameter 0.50 mm, and inner diameter 0.15 mm). After each needle was thrust through the rubber wall of the injection part of the tube system, the samples were ready for injection. This was effected by manually pressing the piston of each syringe in succession, emptying each completely within less than 2 seconds. The injected samples are then transported by the carrier stream via the mixing coil into the detector where the ammonia gas generated by the chemical reaction was released in a flow-through chamber and measured, while the carrier stream was led to waste. The length of tubing 28 between the injector and the detector was 1.5 m, which allowed sufficient time for the chemical reaction between the sodium hydroxide of the carrier stream and the ammonium chloride of the samples to reach completion. The detector, a known type of ammonia detector, contained a glass electrode situated above the carrier stream and separated from it by an air-gap of ca. 2 mm thickness (see Danish patent application No. 3757/73, Int.kl. Goln). The ammonia gas released in the detector chamber diffused to the surface of the glass electrode and changed the pH of a thin electrolyte layer of ammonium chloride covering it (in this case the electrolyte solution consisted of 1.0M $NH_4Cl$ and 1.0M NaCl). This change in pH was continuously registered on a recorder and whenever the signal reached maximum, a digital readout (to 0.001 pH) was made. The recorded output as expressed in pH-units as a function of time is shown in FIG. 2a, while the calibration curve based on the digital read-outs is reproduced in FIG. 2b. The most important observations are: (a) the output of the detector is linear, closely following Nernst's law, which confirms that the chemical reactions occur reproducibly in the flowing stream within the segments of the injected samples; and (b) even the manual injection of the samples allows to reach sufficient precision since a computer evaluation of the digital read-outs by linear regression analysis yielded the following data: regression coefficient: 0.99996; and relative standard deviation: 0.0038 pH-units, corresponding to 0.9% in the ammonium concentration (in mol/1) in the samples.

The relative low sampling rate obtained here (as compared with the one stated in Example II) was found to be due to a large "dead volume" of the detector chamber (in which was present ca. 2.3 ml of aqueous solution and ca. 4 ml gas solution, the latter constituting said air-gap); therefore a spectrophotometric determination was chosen as the next example on the application of the present invention.

EXAMPLE II

Automated spectrophometric determination by means of the sample injection principle.

The carrier stream consisted of a $2.0\times10^{-1}$M solution of HCl which was pumped at a rate of 20 ml per minute through a tubing system of internal diameter 1.5 mm by means of a peristaltic pump. Following the pump was placed an injection unit similar to the one described in Example I (although the rubber tube in this experiment was replaced by a length of silicone rubber tubing of internal diameter 1.5 mm and of a wall thickness of 2.5 mm). The carrier stream proceeded from the injector through a polyethylene tube (internal diameter 1.5 mm, wall thickness 1 mm) which in this case served both as the mixing tubing (for practical reasons wound into a coil) and as the transmission part, having a total length of 2.5 m of which the transmission tubing constituted 0.4 m. A Beckman DB-GT grating spectrophotometer, equipped with a tubular flow-cell (optical path length 10 mm and volume 0.080 ml) was used as detector. The optical density (absorbance) of the carrier stream was continuously recorded, monitoring at a wavelength of 510 mm. The samples (volumn 0.50 ml), consisting of methyl orange in $1.0\times10^{-3}$M NaOH (concentrations: $25\times10^{-4}$%; $12.5\times10^{-4}$%; $6.25\times10^{-4}$%; $3.125\times10^{-4}$%; and $1.563\times10^{-4}$%; respectively), were injected manually into the carrier stream by means of disposable syringes in the same manner as described in Example I.

Figure 3A:
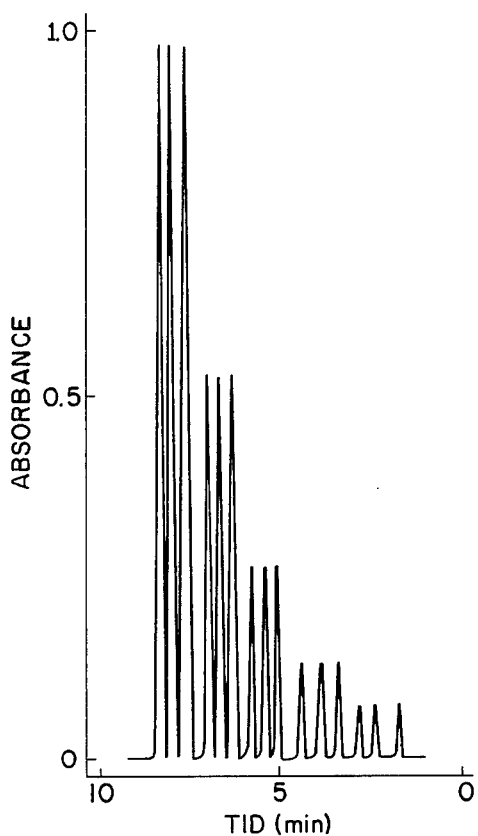
Figure 3B:
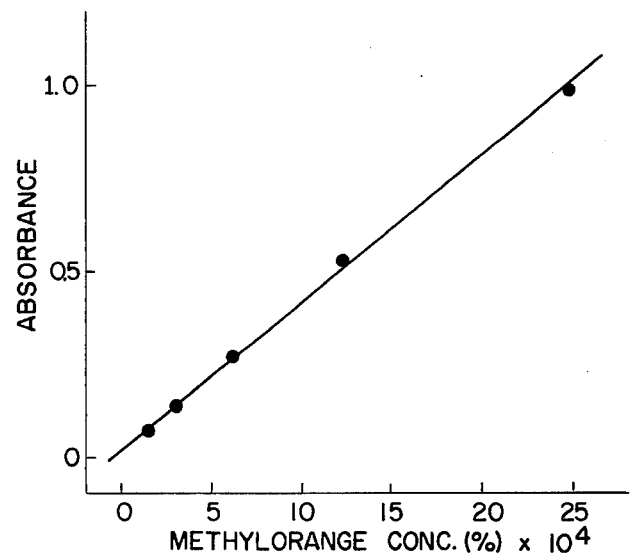
Figure 3C:
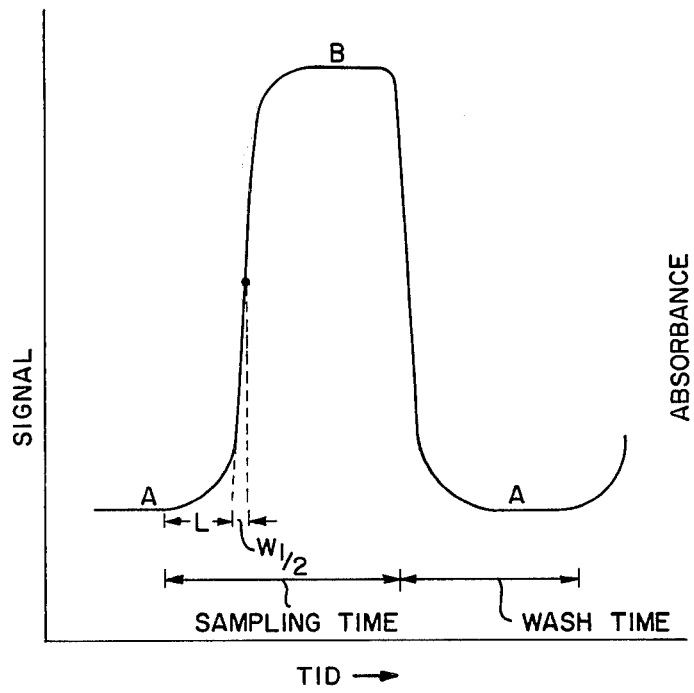
Figure 3C:
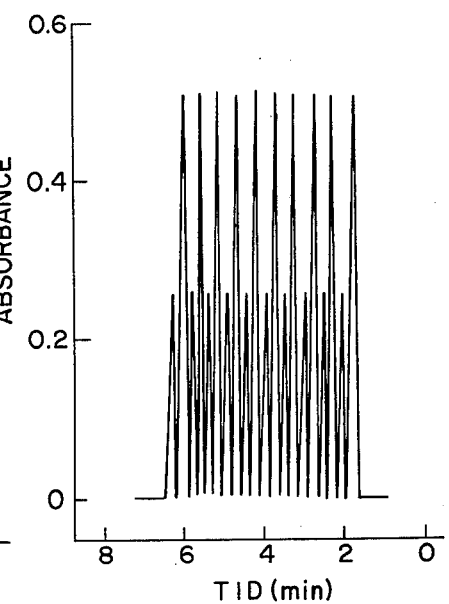

After injection into the carrier stream the alkaline samples became acid and the yellow colour characteristic for methyl orange in alkaline medium turned into the red coloured acid from which colour then was quantitatively measured and the signals reproduced as peaks on an attached recorder. Thus, not only the geometry of the sample segments, but also the acidobasic equilibria taking place within the carrier stream are reflected by the output signals. The continuous recording of the optical density in absorbance units (as registered on the recorder) versus time is shown in FIG. 3a, while the calibration curve, as obtained by plotting the height of the recorded peaks versus concentration of methyl orange in the samples, is shown in FIG. 3b. Due to the narrower diameter of the tubing system used, a faster flow of the carrier, and a much smaller dead volume in the detector unit (that is, in the flow-through cell), a much faster sampling rate (compared to the one denoted for the system described in Example I) could be achieved well in excess of 200 samples per hour (see FIG. 3c which shows a sampling capacity of ca. 270 samples per hour — and that is even obtained by manual sample introductions). The most important observations in this experiment are: (a) The output of the detector closely follows the Lamber-Berr's law, being linear within the expected range (since the registrations on the recorder are the basis for the calculations of the calibration curves shown herein, the time constant of the recorder might very well determine the accuracy with which the signal output can be registered at higher concentrations; in fact, it was established that at methyl orange concentrations of $2.5 \times 10^{-4}\%$ the recorder used — a Servogor RE 511 — was indeed too slow, that is, the "true" calibration curve is actually better than the one reproduced in FIG. 3b); (b) The manual injection of the samples allows the attainment of a very high degree of precision, which in the actual case, i.e., for the calibration curve depicted in FIG. 3b, is manifested by a calculated regression coefficient of 0.9993 and a relative standard error of 0.01 absorbance-units, corresponding to ca. 2% in the concentration of methyl orange (and this error is to a great extend very likely due to what was mentioned above as to the recorder unit — since relative standard errors later, with another recorder, generally were found to be below 1%), which is more than sufficient for any spectrophotometric assay; (c) The improved flow and detector geometry allows an unpredendented sampling rate to be achieved, thus confirming the advantageous aspect of the discrete, instant sampling technique; (d) The non-airsegmented carrier stream has, due to its incompressibility, no inertia which, unlike the airsegemented system, allows the apparatus to be used immediately after the pumping action has been initiated. Thus an "always ready" system is available as there is no appreciable change in the calibration curve after short or long periods of pumping.

In view of the foregoing, it is evident that the discrete, instant sampling technique allows continuous analysis to be carried out in a new, much simplified manner which at the same time permits a large number of samples to be analyzed within a short span of time. If non-airsegmented streams are used, the apparatus has practically no inertia which allows its immediate use, thus making it ready for operation at any time. After a required number of analyses has been rapidly executed, the pumping action can be stopped again. Thus, not only expenditures for reagents but also operator's time is saved. Alternatively, an unprecendented large number of analyses can be executed within a working day. By using disposable syringes a good economy of operation, comparable with other automated systems, can be achieved. As long as that identical volumes of sample are used, that the samples are introduced into the carrier stream within the same (preferably short) span of time, and that the carrier stream is flowing at the same rate, the heights of the recorded peaks are proportional to the concentrations of the assayed substances, provided that the chemical reaction taking place always advances to the same degree (for instance to 100%) and that the output of the detector is linear. Theoretically it is the area under the recorded peaks which is proportional to the concentration; however, since the individual peaks are congruent, the concentration will therefore also be proportional to the peak-heights. For various reasons this assumption might, however, prove too coarse — i.e., the recorder might have a larger time constant than the detector unit — and in such cases the problem may generally be solved by measuring the area under the individual peaks, that is, in practice to also provide an integrator.

It should be made clear that although the injection of samples into a flowing medium has been described for the purpose of liquid chromatography, the purpose of that technique is to separate the components of the sample by letting it pass through a column, packed with solid particles, on the surface of which the separation is effected. Furthermore, the liquids pass through these columns slowly and their flow is obstructed by the material with which the columns are packed.

Although several embodiments of the invention have been disclosed herein for the purposes of illustration, it will be understood that further variations and modifications of the structures, materials and uses disclosed and discussed herein may be made without departing from the spirit of the invention the scope of which is defined by the following claims.

What is claimed is:

1. Method of continuous flow analysis of a liquid sample in a carrier stream, said method comprising the steps of:
    forming said carrier stream as a continuous unobstructed flow of liquid in a tube, said flow being turbulent at a predetermined station within said tube and
    injecting said sample through a wall of said tube into said stream as a discrete volume at or upstream from said station.

2. Method as defined in claim 1 wherein said step of injecting is carried out at a rate in excess of about 3 ml/min. for not more than about 20 seconds.

3. The method as defined in claim 1 including the step of pumping said stream past said station, said carrier stream being pumped so rapidly and said stream being of such small cross section area that the flow of said stream, at least in the portion thereof beyond said station, is turbulent.

4. Method as defined in claim 3 including the step of detecting, downstream of said station, results of reaction between said carrier and said sample.

5. Method as defined in claim 4 wherein said carrier stream is formed to contain chemical compounds intended to react with said sample so as to provide a change in the optical density of said carrier stream at a position downstream of said station.

6. Method as defined in claim 4 wherein said carrier stream is formed to contain chemical compounds intended to react with said samples so as to provide reaction products which can be continuously monitored by an electrochemical sensor.

7. Apparatus for continuous analysis of a sample solution in a carrier stream, said apparatus comprising in combination;
    means providing a continuous unobstructed liquid carrier stream;
    a flexible walled tubular conduit;
    means for pumping liquid from said source through said conduit so that the flow through at least a portion of the latter is substantially turbulent; and means for injecting a predetermined volume of said sample solution through a wall of said flexible conduit and into the carrier stream within said conduit upstream of or in said turbulent flow.

8. Apparatus as defined in claim 7 including means for detecting the results of reaction between said carrier stream and said sample solution at a position downstream from the point of injection of said sample solution.

9. Apparatus as defined in claim 8 wherein said means for injecting comprises a cannulus adapted to pierce said wall, and means for expressing said volume of sample solution through said cannulus and into the interior of said tube.

* * * * *